(12) United States Patent
Davies et al.

(10) Patent No.: US 6,197,296 B1
(45) Date of Patent: *Mar. 6, 2001

(54) TISSUE EQUIVALENTS

(75) Inventors: Alban Davies, York; Sarah Haynes, Keele, both of (GB); Tom Browne, Perth (AU); John Kearney, Wakefield (GB)

(73) Assignee: National Heart Research Fund, Leeds (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/343,432

(22) PCT Filed: Mar. 29, 1994

(86) PCT No.: PCT/GB94/00659

§ 371 Date: Jul. 21, 1997

§ 102(e) Date: Jul. 21, 1997

(87) PCT Pub. No.: WO94/22505

PCT Pub. Date: Oct. 13, 1994

(Under 37 CFR 1.47)

(30) Foreign Application Priority Data

Mar. 29, 1993 (GB) .................................................. 9306449

(51) Int. Cl.⁷ ...................................................... C12N 5/08
(52) U.S. Cl. ........................... 424/93.7; 623/11; 623/12; 623/1
(58) Field of Search .............................. 424/93.7; 623/11, 623/12, 1

(56) References Cited

U.S. PATENT DOCUMENTS

| | | | |
|---|---|---|---|
| 3,272,204 | 9/1966 | Artandi et al. | 128/334 |
| 3,400,719 | 9/1968 | Eckhart | 128/334 |
| 4,546,500 | 10/1985 | Bell | 623/1 |
| 4,721,096 | 1/1988 | Naughton et al. | 128/1 R |
| 4,963,489 | 10/1990 | Naughton et al. | 435/1.1 |
| 5,032,508 | 7/1991 | Naughton et al. | 435/32 |
| 5,863,531 | 1/1999 | Naughton et al. | 424/93.7 |

FOREIGN PATENT DOCUMENTS

| | | |
|---|---|---|
| 0393788 | 10/1990 | (EP) . |
| 0418035 | 3/1991 | (EP) . |
| 0457430 | 11/1991 | (EP) . |
| 8203764 | 11/1982 | (WO) . |

OTHER PUBLICATIONS

Foxall, Thomas L., et al., "Adult Human Endothelial Cell Coverage . . . " *Journal of Surgical Research*, 41, pp. 158–172 (published, Aug. 1986).

Miwa H., et al., "Development of Hierarchically Structured . . . Graft," *Jpn. Artif. Organs*, 22(2):468–472 (published, Feb. 22, 1993).

Kanda K., et al., "A Highly Structured Hybrid Artificial Media, . . . ," *Jpn. Artif. Organs*, 22(2):478–482 (published, Feb. 22, 1993).

K. Kanda et al., "Phenotypic Modulation of Smooth Muscle Cells in Intima–Media . . . " ASAIO Journal, 39(1993) Jul./Sep. 1993, No. 3 pp. M–278–M282.

*Primary Examiner*—Jean C. Witz
(74) *Attorney, Agent, or Firm*—Edwin D. Schindler

(57) ABSTRACT

A method of forming a tissue equivalent is described. A length of polyester tube is threaded over a mandrel (H) and attached at either end by clips at A and D. A block (F) is then screwed into place. The polyester is then pre-soaked by injecting through Tap (2) an acidified collagen solution for approximately one hour. After a suitable period of time the excess solution is aspirated off. Following this stage, a second, alkaline solution is injected into the apparatus which contains smooth muscle cells (SMC). Thus, neutralisation of the collagen impregnated within the fabric of the tube occurs leading to spontaneous fibrillogenesis within the interstices of the cloth, eliminating the risk of delamination. The apparatus is then incubated. The collagen contracts down onto the fabric tube and the cell-impregnated gel becomes incorporated into the presoaked collagen. The pre-impregnated collagen and the collagen provided in the aqueous mixture contract down as one into a coherent whole with the SMC. The tissue equivalent is then lined with endothelial cells and the apparatus again incubated and fed at increasing intraluminal pressures applied either statically or dynamically. This is believed to cause the vessel to become preconditioned to the pressure it will work under as an implant. This allows organization of the basement membrane which in turn promotes EC attachment and theoretically prevents smooth muscle cell hyperplasia.

5 Claims, 1 Drawing Sheet

TISSUE EQUIVALENTS

INTRODUCTION

This invention is concerned with the creation of tissue equivalents and methods for their preparation. Although reference will be made hereinafter to the preparation of vascular grafts, it should be understood that the present invention has applications to various other tissue equivalents, for instance heart valves. The invention has application to a suitable implantable or reconstructive material with an active cellular lining, for example endothelial, whether autologous or not.

BACKGROUND TO THE INVENTION

There are a number of clinical situations in which implants are required. A vascular graft may be desirable in order to replace a section of vessel damage during trauma, or to bypass vessels exhibiting occlusive diseases, for instance, for coronary artery bypass. The two major alternatives available for vascular grafting are the use of an autologous vessel from elsewhere in the body, or the use of biological or synthetic prostheses. Both alternatives have drawbacks. The former may be surgically time consuming and availability limited. Prosthetic materials, while surgically convenient, have a number of performance disadvantages.

Coronary artery bypass grafting remains the most effective longer term treatment for coronary artery disease. Since the introduction of the bypass technique, many different types of vascular grafts have been evaluated. The most obvious source of a vascular conduit is autologous vein or artery removed or transposed from elsewhere in the body. Saphenous vein and internal mammary artery have been used. Saphenous vein conduits suffer from early thrombotic occlusion and also from late failures so that more than 50% have occluded by 10 years. A major drawback with the use of autologous material is that, when occlusion does occur, there is often insufficient autologous conduit left for re-operations. This is particularly relevant when multiple bypass operations are required. Alternatively, saphenous vein may be unavailable, for instance, due to varicosities.

Artificial prostheses constructed from such diverse materials as woven Dacron™, Gore-Tex™ and expanded microporous polytetrafluoroethylene all suffer to a greater or lesser extent from thrombus formation. Attention has therefore turned towards biological grafts of non-autologous origin.

Allograft veins and arteries from post mortem donors have been used with variable success. However, reliance on this source is unlikely to fulfil demand. To overcome this availability problem, the use of human umbilical veins and arteries has been considered. Unfortunately, these have exhibited poor mechanical performance and rapid occlusion.

Following the successful use of glutaraldehyde preserved animal valves in valve replacement surgery, many groups turned to xenografts as a possible source of vascular replacements. Xenografts need to be chemically modified in order to decrease immunogenicity and increase resistance to resorption. Glutaraldehyde has been the commonest crosslinking agent used. However, its side effects include cytotoxicity which could inhibit endothelial re-colonisation and increased stiffening leading to kinking and a lack of stretch and elasticity. When a less severe crosslinking regimen was used, using aldehyde vapour, only a temporary resistance to degradation was seen. This is likely to lead to an increased risk of aneurysm formation.

U.S. Pat. No. 4,546,500 discloses the preparation of a vessel equivalent from a series of layers of gel contracted from aqueous mixtures of collagen fibrils, a nutrient medium and smooth muscle cells or fibroblast cells. In addition, it has been suggested to include a Dacron™ mesh between two layers of the multi-layer structure. The addition of a second layer of collagen resulted in a multi-laminated structure in which the mechanical strength was provided by the Dacron™ alone. These blood vessel equivalents, constructed from several layers of collagen and Dacron™, have been shown to suffer from delamination problems. The use of fibrin as a biological glue to adhere the collagen layers together has since been employed. It is an object of this invention to overcome this problem.

In addition, it is an object of this invention to improve the preconditioning of the tissue equivalents to the pressures—e.g. blood pressure—to which it will be subjected within the body.

SUMMARY OF THE INVENTION

According to a first aspect of the present invention, there is provided a method of forming a tissue equivalent comprising impregnating a fibrous substrate with collagen fibrils, applying to the impregnated substrate an aqueous mixture of collagen fibrils, a nutrient medium and a cellular contractile agent, and incubating the system to allow a gel to form from the aqueous mixture and to contract and express aqueous medium therefrom. By pre-impregnating the fibrous substrate with solubilised collagen, followed by casting a single collagen gel, the problems of delamination are avoided. Using the process of the present invention, collagen has been shown to infiltrate and interweave within the synthetic structure and to be reorganised within it an a coherent whole. The preferred fibrous substrate is Dacron™ fabric.

The fibrous substrate may be impregnated by soaking in an acidic aqueous collagen solution. This is preferable as it holds the collagen in solution during the impregnation. Subsequently, an alkaline aqueous mixture of collagen fibrils, a nutrient medium and a cellular contractile agent may be applied to neutralise the acidic impregnation of the substrate and initiate collagen fibrillogenesis. The cellular contractile agent will usually comprise smooth muscle cells.

Thrombogenicity may be prevented by covering the tissue equivalent with a monolayer of functional endothelial cells (EC). The attachment and activity of these cells may be enhanced by their interaction with the underlying SMC populated collagen matrix, resulting in the formation of basement membrane.

According to a second aspect of the present invention, there is provided a method of forming a tissue equivalent comprising forming a contracted gel from an aqueous mixture of collagen fibrils, a nutrient medium and a cellular contractile agent, lining the tissue equivalent with endothelial cells, applying an aqueous fluid under pressure to the face or faces of the tissue equivalent lined with endothelial cells and preconditioning the tissue equivalent by incubating the system whilst increasing the pressure applied to the said face or faces of the tissue equivalent. The endothelial cells applied to a tissue equivalent formed in accordance with the first aspect of the invention may be applied in this way. By using hydrostatic and/or hydrodynamic preconditioning, the remodelling of the collagen fibrils can be influenced. In this way, the alignment of the resulting fibres may be of structural importance as they tend to align in such a way as to account for the stresses imposed by the pressurised fluid.

The lining of the tissue equivalent with endothelial cells may involve exposing it to cultured endothelial cells in a cell support medium. Similarly, the pressurised may be an endothelial support medium.

BRIEF DESCRIPTION OF THE DRAWINGS

The present invention will now be described by way of example with reference to the accompanying drawing of apparatus upon which a vessel equivalent may be formed.

DETAILED DESCRIPTION

Figure 1:
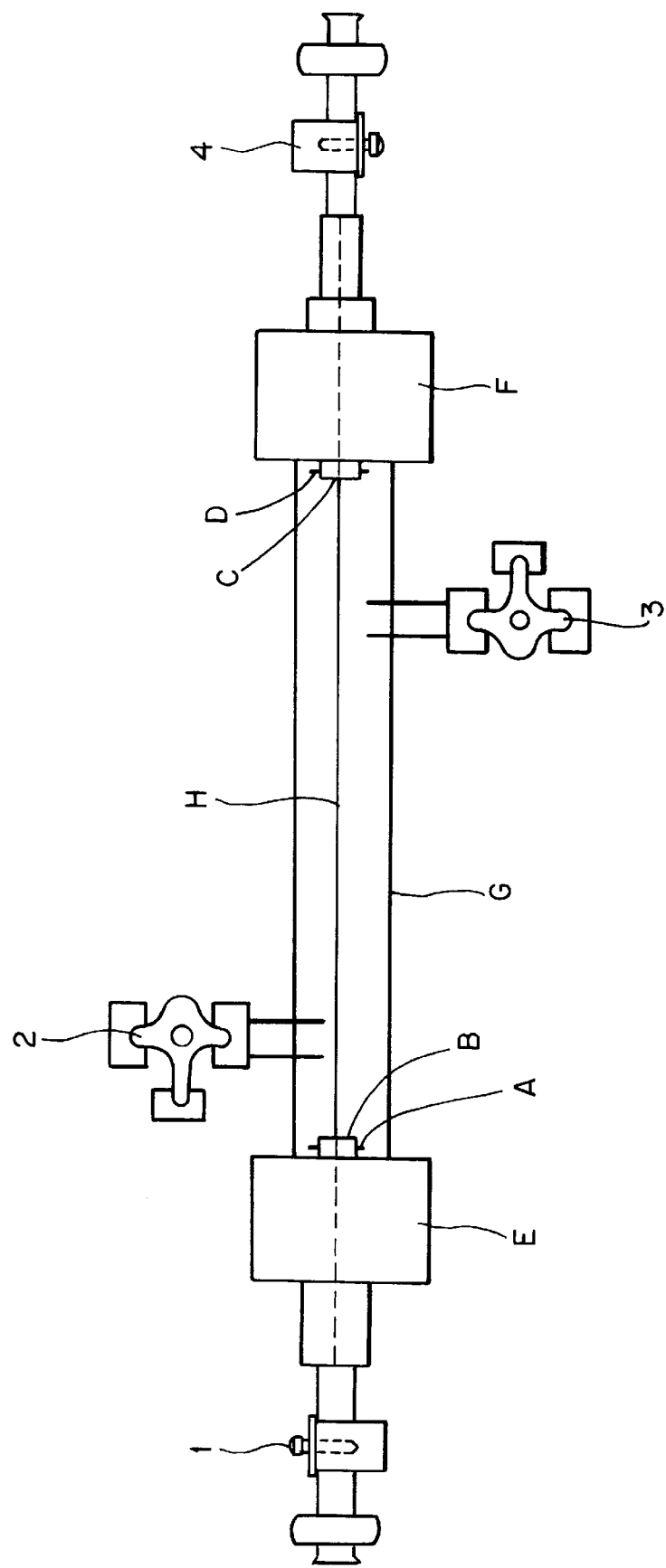

The present invention, in its application to vascular grafts, is concerned with the production of material having improved performance characteristics which is suitable for use in a variety of clinical indications, including coronary bypass surgery, and which is also surgically convenient.

To produce a vascular graft in accordance with the presently described example of the invention, a tube is constructed from human vascular cells, extracellular matrix macromolecules, and a synthetic polymer such as polyester. This fabrication process makes use of the ability of vascular smooth muscle cells to remodel and reorganise anhydrated type I collagen gel into a tissue-like material. By combining this "living tissue" with a synthetic tubular framework, and subsequently lining the lumen with functional endothelium, a viable vascular graft may be formed. Ideally, for a graft to be successful, it must be non-immunogenic, non-thrombogenic and biocompatible. It must also be able to withstand intraluminal pressures in the order of 300 mmHg whilst maintaining its structural integrity, i.e. it must not leak or form aneurysm.

By using autologous cells, problems of immunogenicity are circumvented. However, it is also possible to use allogenic cultured cells without eliciting a graft-specific immune response. The collagen used may be extracted from rat tail tendons, in the form of an acid solubilised solution, or commercially available collagen powders. This collagen solution is combined with serum, culture medium and smooth muscle cells (SMC) to form the casting solution. None of these constituents will be significantly immunogenic. Neutralisation of the casting mixture induces fibrillogenesis of the collagen and the formation of a gel. The collagen is subsequently reorganised and structured into thicker fibres through the action of the SMC.

Biocompatibility refers to the synthetic element of the proposed graft. By using medical grade materials, this is not a problem. The biological component of the composite, i.e. the collagen/SMC matrix, is the most vulnerable to degradation. Experimental evidence indicates that the collagen matrix becomes increasingly resistant to collagenase digestion as time in culture progresses. This indicates crosslinking of the collagen by the cell dependent reorganisation process. Further crosslinking, using chemical agents may be carried out.

The cells utilised in this invention may be autologous or otherwise and are cultured using standard cell culture techniques. Additions to the standard solutions for the gel matrix may include various proteoglycans e.g. Chrondroitin 6 Sulphate, and/or Hyaluronic acid. The culture solutions may be varied. Accepted sterile techniques should be utilised throughout.

The mechanical strength of the composite graft is derived from two sources: the synthetic support; and the collagen matrix. By means of a method of the present invention, it is possible to construct a small calibre vascular graft, or indeed larger grafts, with a functional endothelium. The structure of this graft consists of a living component (collagen/SMC/EC) and a non-living synthetic element. This graft is a true composite, both components providing the mechanical strength. This approach is in contrast to known methods in which a Dacron™ sleeve is added to the first layer of collagen after the collagen reorganisation was completed.

The presence of living endothelial cells on the vessels internal surface, which actively produce substances able to prevent thrombosis formation has major advantages to graft patency. The collagen/SMC matrix mimics the sub-endothelial layer of blood vessel walls, thus providing a structure for anchoring the endothelial cells to the vessel wall. Such a composite allows the formation of a functional basement membrane. We believe that: the basement membrane is important not only in allowing lining regeneration after injury but also in protecting against smooth muscle cell hyperplasia which reduces vessel patency.

EXAMPLE

The following description relates to a preferred method of creating a tubular vessel equivalent. The apparatus of FIG. 1 is currently being employed—but many variations could be made by one of ordinary skill in the art to the basic design without departing from the invention. This example creates a craft which will not delaminate.

The dimensions of the apparatus vary depending on the diameter and length of graft required. The apparatus should be made of a material which can be sterilised without becoming opaque. The apparatus consists of a Perspex™ chamber G sealed at its ends by blocks E & F, presently made from Delrin™. The central mandrel H may be of any non-toxic non-degradable material—for very small diameters a non-absorbable suture may be used but it must not adhere to the gel. It is a temporary support for the graft. The 3-way taps 1, 2, 3 and 4 are of medical grade.

Once the apparatus has been sterilised block F is unscrewed and a suitable length of polyester tube of the required diameter is threaded over mandrel H and attached at either end by clips at A & D. F is then screwed back into place. In this description knitted Dacron™ polyester material is used, made by Vascutek Limited, Renfrewshire, Scotland. Various materials woven or knitted of implant grade—sterile and bio-compatible—may be used.

Once the Dacron™ is in place it is then pre-soaked by injecting through Tap 2 an acidified collagen solution for approximately one hour—though the timing is not critical. The solution contains purified collagen at 1 mg/ml of 1:1000 acetic acid solution. This; concentration may be varied. After such a period of time the excess solution is aspirated off. This technique ensures impregnation of the fabric tube.

Following this stage, a second solution is injected into the apparatus which contains smooth muscle cells (SMC). The passage number of the cells may be varied as they may also be for the endothelial cells (EC) discussed below. The seeding concentration of the cells may also be varied which allows faster or slower concentration time. The seeding density described below used $3.3 \times 10^4$ per 5 mls of matrix solution.

The matrix solution contains 36 mls×2 Dulbecco's Modified Eagles Medium (DMEM). In all, 9 mls Pooled Human Serum, 9 mls 0.1 M NaOH, 27 mls Collagen at 3.3 mg/ml and 9 mls of SMC were present in 1 unit of DMEM. The nutrient medium may be altered from the above and it is within the ability of one of ordinary skill in the art to do so.

Solution may also be injected into the lumen by manipulating taps 1 & 4. Thus, neutralisation of the collagen impregnated within the fabric of the tube occurs leading to spontaneous fibrillogenesis within the interstices of the cloth, reducing the risk of delamination. The apparatus is then incubated at 37° C. using standard cell culture devices. After 3–5 days depending on cell concentration for example, the collagen contracts down onto the fabric tube and the cell-impregnated gel becomes incorporated into the pre-soaked collagen. The pre-impregnated collagen and the collagen provided in the aqueous mixture contract down as one into a coherent whole with the SMC.

Nutrient Medium, e.g. DMEM, together with human serum with or without foetal calf serum, will be added to the apparatus every 3–5 days to maintain the cells and matrix after the existing solution has been drained off. After a period of approximately 21 days—again varying with temperature and cell seeding density, collagen concentration etc., the matrix will have contracted sufficiently for the next stage, which is endothelial seeding.

Standard cultured endothelial cells, of variable cell lines and passage number,, are then added to the inside of the tube after being mixed with a standard endothelial support medium which includes heparin, human and foetal calf serum and endothelial cell growth factors. Endothelial seeding density may vary but in this example $5 \times 10^4$ per cm$^2$ is used. The apparatus is then gently rolled and agitated to spread the EC's on the luminal surface for a variable but noncritical time span.

The apparatus is then again incubated and a confluent monolayer of EC's obtained within usually one week. Standard endothelial support medium with its growth factor etc., will be exchanged with the existing fluid every few days. A basement membrane is thus created within a short period of time. The vessel is kept incubated for a relatively short period of time, e.g. one week, and fed at increasing intraluminal pressures applied either statically or dynamically. For example a peristaltic pump may circulate the support medium in a close loop at the required pressures. We believe that this causes the vessel to become preconditioned to the pressure it will work under as an implant. This allows organisation of the basement membrane which in turn promotes EC attachment and theoretically prevents smooth muscle cell hyperplasia.

Such a graft may then be implanted or cryopreserved using standard Cyopreservation techniques. In addition, the exterior of the tissue equivalent may be sealed with biological glue.

The essentials of the two aspects of this invention are the two stage casting of the extracellular gel into and on the Dacron™ fabric and the preconditioning of the graft. The nature and constituents of the solutions may readily be varied and within the standard knowledge of cell culture techniques are not in themselves critical.

What is claimed is:

1. A method for forming and preparing for use a tissue equivalent, comprising the steps of:
    forming a contracted gel from an aqueous mixture of collagen fibrils, a nutrient medium and a cellular contractile agent;
    lining the contracted gel with endothelial cells, thereby obtaining a tissue equivalent;
    applying an aqueous fluid under pressure to at least one face of said tissue equivalent; and,
    preconditioning said tissue equivalent by incubation, while increasing the pressure applied to said at least one face of said tissue equivalent, said preconditioning taking place only after completion of said lining the contracted gel with endothelial cells to obtain said tissue equivalent.

2. The method for forming and preparing a tissue equivalent according to claim 1, wherein said step of lining the contracted gel with endothelial cells comprises exposing the contracted gel to cultured endothelial cells in a cell support medium.

3. The method for forming and preparing a tissue equivalent according to claim 1, where the pressure applied is hydrostatic.

4. The method for forming and preparing a tissue equivalent according to claim 1, wherein said aqueous fluid flows under pressure across said at least one face of said tissue equivalent.

5. The method for forming and preparing a tissue equivalent according to claim 1, wherein said aqueous fluid is an endothelial support.

* * * * *